United States Patent
Imamura

(10) Patent No.: US 8,678,783 B2
(45) Date of Patent: Mar. 25, 2014

(54) SOLUTION SENDING PUMP

(75) Inventor: Shinya Imamura, Osaka (JP)

(73) Assignee: Shimadzu Corporation, Kyoto (JP)

( * ) Notice: Subject to any disclaimer, the term of this patent is extended or adjusted under 35 U.S.C. 154(b) by 551 days.

(21) Appl. No.: 12/984,979

(22) Filed: Jan. 5, 2011

(65) Prior Publication Data

US 2011/0164996 A1 Jul. 7, 2011

(30) Foreign Application Priority Data

Jan. 6, 2010 (JP) ................................ 2010-000894

(51) Int. Cl.
- *F04B 35/00* (2006.01)
- *F04B 17/00* (2006.01)

(52) U.S. Cl.
USPC .......................................... 417/363; 417/360

(58) Field of Classification Search
USPC .......... 417/360, 362, 363, 415; 248/638, 612, 248/613, 674; 310/51, 91
See application file for complete search history.

(56) References Cited

U.S. PATENT DOCUMENTS

| | | | | |
|---|---|---|---|---|
| 1,998,338 A | * | 4/1935 | Spohrer | 137/565.18 |
| 2,735,611 A | * | 2/1956 | McLean | 417/362 |
| 2,838,262 A | * | 6/1958 | Anderson | 248/603 |
| 2,928,961 A | * | 3/1960 | Morrill | 310/91 |
| 3,395,594 A | * | 8/1968 | Balair | 74/606 R |
| 4,104,007 A | * | 8/1978 | Hehl | 417/360 |
| 4,123,968 A | * | 11/1978 | Malott | 454/354 |
| 4,200,257 A | * | 4/1980 | Litch, III | 248/604 |
| 4,425,813 A | * | 1/1984 | Wadensten | 74/87 |
| 4,452,417 A | * | 6/1984 | Krafthefer et al. | 248/604 |
| 4,648,579 A | * | 3/1987 | Wilson | 248/638 |
| 4,655,099 A | * | 4/1987 | Hansen | 74/421 A |
| 5,051,636 A | * | 9/1991 | Ishimoto et al. | 310/90 |
| 5,126,607 A | * | 6/1992 | Merriman, Jr. | 310/51 |
| 5,291,967 A | * | 3/1994 | Aoki | 180/312 |
| 5,354,182 A | * | 10/1994 | Niemiec et al. | 417/363 |
| 5,431,457 A | * | 7/1995 | Youngs | 285/136.1 |
| 5,551,843 A | * | 9/1996 | Hauser | 417/234 |
| 5,566,494 A | | 10/1996 | Zimmer | |
| 5,884,893 A | * | 3/1999 | Seki et al. | 248/638 |
| 6,125,726 A | * | 10/2000 | Vendetti et al. | 81/447 |

(Continued)

FOREIGN PATENT DOCUMENTS

| | | |
|---|---|---|
| CN | 1104811 A | 7/1995 |
| CN | 2354914 Y | 12/1999 |

(Continued)

OTHER PUBLICATIONS

The First Office Action for the Application No. 201110009940,3 from The State Intellectual Property Office of the People's Republic of China dated Jan. 31, 2013.

(Continued)

*Primary Examiner* — Charles Freay
*Assistant Examiner* — Alexander Comley
(74) *Attorney, Agent, or Firm* — Cheng Law Group, PLLC

(57) ABSTRACT

A motor is fixed to a retaining member by bolts and well nuts. The well nuts are attached to the retaining member so that their flange portions are positioned between a motor fixing portion and the retaining member, and a clearance corresponding to thickness of the flanges of the well nuts is provided between the motor fixing portion and the retaining member. Heat-conductive elastic members are sandwiched between the motor fixing portion and the retaining member.

2 Claims, 4 Drawing Sheets

(56) References Cited

U.S. PATENT DOCUMENTS

| | | | |
|---|---|---|---|
| 6,234,445 B1* | 5/2001 | Yoon | 248/638 |
| 6,328,274 B1* | 12/2001 | Hayashi | 248/638 |
| 6,557,816 B2* | 5/2003 | Yoshida | 248/674 |
| 6,866,486 B2* | 3/2005 | Dexter et al. | 417/299 |
| 7,422,421 B2 | 9/2008 | Sakai | |
| 2002/0175264 A1* | 11/2002 | Trago et al. | 248/637 |
| 2005/0260104 A1* | 11/2005 | Culbert et al. | 422/121 |
| 2006/0127234 A1* | 6/2006 | Sakai | 417/273 |
| 2006/0228233 A1* | 10/2006 | Cook | 417/360 |

FOREIGN PATENT DOCUMENTS

| | | | |
|---|---|---|---|
| CN | 2746150 Y | 12/2005 | |
| JP | 7-318548 A | 12/1995 | |
| JP | 2004-173352 * | 6/2004 | 310/91 |
| JP | 2004-173352 A | 6/2004 | |
| JP | 2004-278995 A | 10/2004 | |
| JP | 2006-161772 A | 6/2006 | |

OTHER PUBLICATIONS

Notification of Reasons for Refusal for the Application No. 2010-000894 from Japan Patent Office mailed Mar. 5, 2013.

* cited by examiner

SOLUTION SENDING PUMP

BACKGROUND OF THE INVENTION

1. Field of the Invention

The present invention relates to a solution sending pump including a pump head having a pump chamber inside itself, a plunger for reciprocating with its tip end inserted into the pump chamber, and a driving portion having a motor for driving the plunger.

2. Description of Background Technique

As a solution sending pump used for sending a solution such as mobile phase in liquid chromatograph, there is a commonly used pump formed to convert rotary movement of a motor into reciprocating movement in a certain direction by a cam mechanism to drive plungers (see Japanese Patent Application Laid-Open No. 7-318548, for example).

Tip ends of the plungers are inserted into pump chambers provided in pump heads and the solution is taken in and discharged by sliding the plungers in the pump chambers. In such a solution sending pump, the plungers, the motor, the cam mechanism are retained by a retaining member and integrated with each other. The retaining member is, for example, an aluminum die-cast product.

If a motor main body is in direct contact with the retaining member, vibration at the time of driving of the motor is transmitted to the plungers through the retaining member and influences operation of the plungers. To cope with this, blind nuts made of rubber are used to fix the motor and the retaining member while separating them from each other or a vibration absorbing rubber for absorbing vibration is sandwiched between the motor and the retaining member.

Besides the problem caused by the vibration, heat radiating effect for suppressing increase in motor temperature when the motor is driven for a long time or driven at high speed is not sufficient in the prior-art structure and the motor temperature increases to a high temperature, which reduces performance. This happens because the blind nuts or the vibration absorbing rubber interposed between the motor and the retaining member prevents transmission of heat of the motor to the retaining member, though the retaining member may have a heat radiating function. High surface temperature of the motor decreases motor longevity and performance to thereby reduce solution sending accuracy.

SUMMARY OF THE INVENTION

It is, therefore, an object of the present invention to provide a solution sending pump which can prevent decrease in longevity and performance caused by heat generation by the motor.

The invention is a solution sending pump including: a pump head having a pump chamber in itself, and solution inlet and outlet for drawing and discharging a solution into and out of the pump chamber; a plunger having a tip end inserted into the pump chamber and for sliding in the pump chamber; a driving portion including a motor for driving the plunger and a driving transmitting portion for converting rotary movement of the motor into reciprocating movement in a certain direction to transmit the movement to the plunger; and a retaining member made of heat-conductive material and for retaining the driving portion. The motor is fixed to the retaining member with a clearance between a main body portion of the motor and the retaining member, the motor main body and the retaining member are fixed to each other by a well nut and a screw, the clearance between the main body portion and the retaining member is defined by a thickness of a flange portion of the well nut, and a heat-conductive elastic member is inserted into the clearance.

In the solution sending pump according to the invention, the motor is fixed to the retaining member with the clearance between the main body portion of the motor and the retaining member, the motor main body and the retaining member are fixed to each other by the well nut and the screw, the clearance between the main body portion and the retaining member is defined by the thickness of the flange portion of the well nut, and the heat-conductive elastic member is inserted into the clearance. Therefore, while vibration of the motor is absorbed by the well nut and the elastic member, heat of the motor is transmitted to the retaining member through the elastic member. In this way, it is possible to improve heat radiating efficiency of the motor without transmitting the vibration of the motor to the driving portion. As a result, reduction in performance caused by heat generation by the motor can be suppressed and solution sending accuracy can be maintained for a long time.

As the retaining member in the invention, an aluminum die-cast product may be used. As the elastic member, a member made of low-molecular siloxane resin may be used.

According to a preferred aspect, a face of the motor main body facing the retaining member is square, the motor main body and the retaining member are fixed to each other at four corner portions of the square, and the elastic member is inserted along each side of the square.

DETAILED DESCRIPTION OF THE INVENTION

Figure 1:
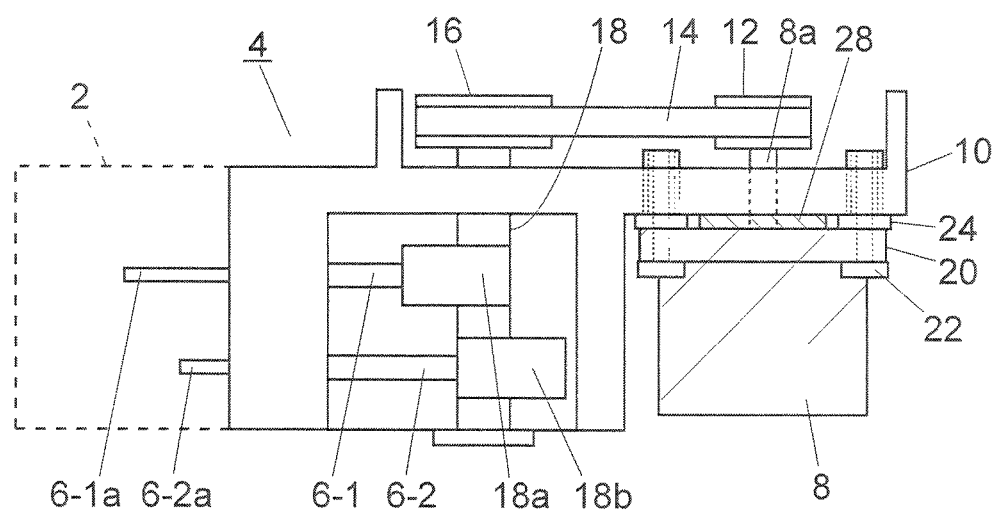
FIG. 1 is a front view of an internal structure of a driving portion of a solution sending device according to an embodiment.

An embodiment of a solution sending pump will be described with reference to FIGS. 1 and 2.

The solution sending pump according to the embodiment is made up of a pump head 2 and a driving portion 4. FIG. 1 shows an internal structure of the driving portion 4 and a concrete example of the pump head 2 will be described later by using FIGS. 3 and 4.

Besides plungers 6-1 and 6-2, the driving portion 4 includes a motor 8 and an aluminum die-cast retaining member 10 for driving the plungers 6-1 and 6-2. Although an internal structure of the pump head 2 is not shown in this drawing, the pump head 2 has two pump heads connected in series as an example. Tip end portions 6-1a and 6-2a of the plungers 6-1 and 6-2 are inserted into pump chambers in the pump heads. When the plunger tip end portions 6-1a and 6-2a slide in the pump chambers, a solution is taken in and discharged at different times in the respective pump chambers to continuously send the solution.

The pump head 2 may include two pump heads connected in parallel or only one pump head.

The motor 8 has, at its upper portion, a motor fixing portion 20 made of aluminum and the motor fixing portion 20 is fixed to the retaining member 10 by bolts 22 and well nuts 24. Each of the well nuts 24 has a cylindrical shape having a flange portion at its one end and is made of chloroprene rubber and an internal thread made of brass is embedded in the other end of the cylinder. The well nut 24 is mounted to the retaining member 10 so that its flange portion is positioned between the motor fixing portion 20 and the retaining member 10. By inserting and fastening the bolt 22 from the flange portion side, an outer diameter of the well nut 24 is increased and, as a result, the well nut 24 is fixed to the retaining member 10 while forming a clearance corresponding to a thickness of the flange of the well nut 24 between the motor fixing portion 20 and the retaining member 10. The well nut 24 is a well nut manufactured by NIPPON POP RIVETS AND FASTENERS LTD., for example.

Furthermore, elastic members 28 having heat conductivity are sandwiched between the motor fixing portion 20 and the retaining member 10. A thickness of the flange portions of the well nuts 24 is, for example, 2 mm and a thickness of the elastic members 28 is greater than that of the flange portions of the well nuts 24 and is 3 mm, for example, when the elastic members 28 are not compressed. Fastened between the motor fixing portion 20 and an aluminum die-cast 24, the elastic members 28 are compressed to 2 mm which is the same as the thickness of the flange portions of the well nuts 24. The elastic members 28 are λ gels manufactured by TAICA CORPORATION, for example.

Figure 2:
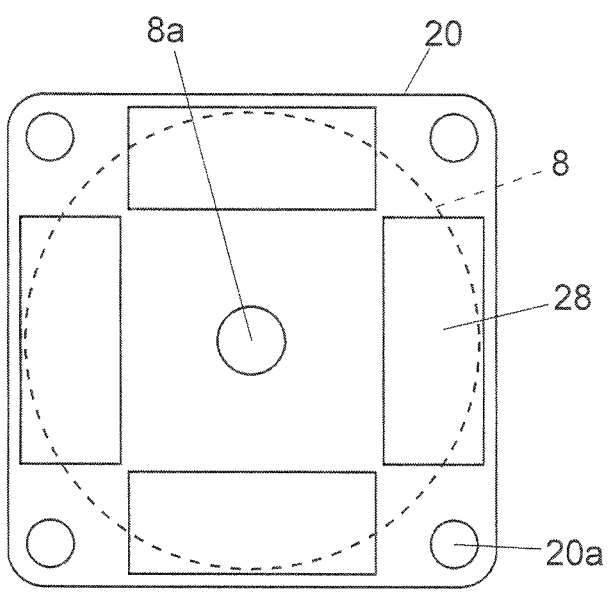
FIG. 2 is a drawing showing a mounted portion of a motor.

The motor fixing portion 20 at the upper portion of the motor 8 has a square planar shape, and through holes 20a through which the bolts 22 are inserted are formed in four corners of the motor fixing portion 20 as shown in FIG. 2. The heat-conductive elastic members 28 are sandwiched along respective sides of the square and in four spaces between the through holes 20a.

Referring back to FIG. 1 to continue description, a driving shaft 8a of the motor 8 passes through a through hole formed in the retaining member 10 and a pulley 12 is attached to a tip end of the driving shaft 8a. The pulley 12 is connected to a pulley 16 by a belt 14 and rotary movement of the driving shaft 8a at the time of driving of the motor 8 is transmitted to the pulley 16.

The pulley 16 is attached to an end of a shaft forming a driving converting portion 18. The driving converting portion 18 has a cam mechanism for converting the rotary movement of the shaft to which the pulley 16 is attached into reciprocating movement in a certain direction. The cam mechanism includes two cams 18a and 18b. Respective base end portions (cross heads) of the plungers 6-1 and 6-2 are in contact with the cams 18a and 18b and the plungers 6-1 and 6-2 reciprocate as the motor 8 rotates.

Figure 3:
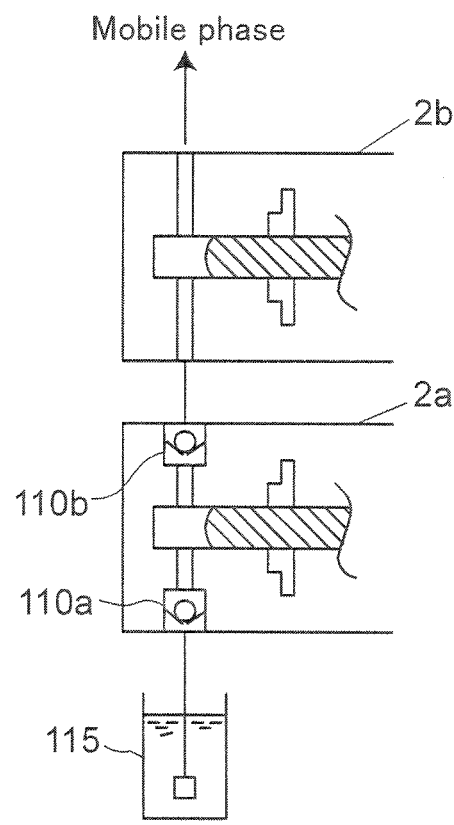
FIG. 3 is a schematic sectional view of pump heads when the present invention is applied to a double-plunger solution sending pump.

FIG. 3 shows an example of the pump head 2 in FIG. 1. The pump head 2 forms, for example, a pump for sending mobile phase to a column in high-speed liquid chromatograph. In this example, the two pump heads 2a and 2b are connected in series to form a double-plunger reciprocating solution sending pump in order to suppress pulsation at the time of sending of the mobile phase. An intake side of the primary pump head 2a is connected to a mobile phase vessel 115 for storing the mobile phase with a check valve 110a interposed therebetween and a discharge side is connected to an intake side of the secondary pump head 2b with a check valve 110b interposed therebetween. A discharge side of the secondary pump head 2b is connected to the column of the high-speed liquid chromatograph.

Figure 4:
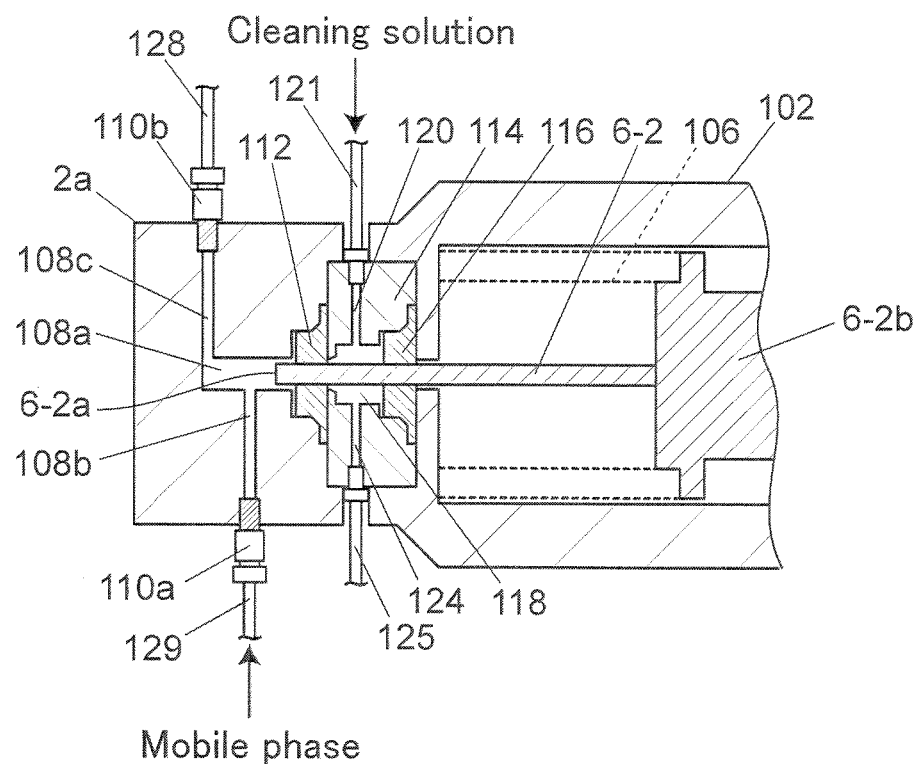
FIG. 4 is a sectional view of a primary pump head out of the pump heads in FIG. 3.

FIG. 4 shows a concrete example of the primary pump head 2a. A structure of the secondary pump head 2b is the same as that of the primary pump head 2a except that it is not provided with check valves, and therefore, the secondary pump head 2b is not shown.

The pump head 2a having, in itself, the pump chamber 108a, an intake flow path 108b, and a discharge flow path 108c is mounted to a tip end of a pump body 102. The pump head 2 in FIG. 1 includes the pump body 102. In the pump body 102, the cross head 6-2b forming the base end portion of the plunger 6-2 is housed and biased by a spring 106 in a direction opposite from the pump head 2a. The plunger 6-2 is retained at a tip end of the cross head 6-2b and the tip end 6-2a of the plunger 6-2 is inserted into the pump chamber 108a.

The cross head 6-2b is caused to reciprocate on a straight line (in a left-right direction in FIG. 4) by a driving mechanism (see FIG. 1) including the cam 18b and, as a result, the plunger 6-2 also reciprocates on the straight line to increase and decrease a capacity in the pump chamber 108a. The intake flow path 108b is connected to a pipe 129, which is connected to the vessel for storing the mobile phase, with the check valve 110a interposed therebetween and the discharge flow path 108c is connected to a pipe 128, which forms an analytical flow path of the liquid chromatograph, with the check valve 110b interposed therebetween.

Between the tip end portion of the pump body 102 and the pump head 2a, a plunger seal 112, a seal holder 114, and a cleaning seal 116 are sandwiched in this order from the pump head 2a side. The plunger seal 112 is for sealing the pump chamber 108a while retaining the plunger 6-2 for sliding at a portion of the pump chamber 108a where the plunger 6-2 is inserted and the plunger seal 112 is supported by the seal holder 114.

The seal holder 114 has, in itself, a cleaning chamber 118 and cleaning chamber flow paths 120 and 124. A pipe 121 for supplying a cleaning solution is connected to the cleaning chamber flow path 120 and a pipe 125 for discharging the cleaning solution from the cleaning chamber 118 is connected to the cleaning chamber flow path 124. The cleaning chamber 118 is sealed with the cleaning seal 116.

As shown in FIGS. 1 and 2, the motor 8 is fixed while separated from the retaining member 10 by the well nuts 24 in the solution sending device in the embodiment, and therefore, transmission of vibration at the time of driving of the motor 8 to the plungers 6-1 and 6-2 through the retaining member 10 is suppressed and an influence of the vibration of the motor 8 on sending of the solution is reduced. Because the heat-conductive elastic members 28 are sandwiched in compressed states between the motor 8 and the retaining member 10, the vibration of the motor 8 is absorbed by the elastic member 28 and heat of the motor 8 is transmitted to the retaining member 10 through the elastic member 28 to thereby increase heat radiating efficiency of the motor 8.

To test the above effects, an experiment for comparing temperatures of the motor 8 with and without the heat-conductive elastic members 28 sandwiched between the motor 8 and the retaining member 10 was performed. In this experiment, an area of an upper face of the motor fixing portion 20 was 3067 mm$^2$ and both a contact area between the elastic members 28 and the motor fixing portion 20 and a contact area between the elastic member 28 and the retaining member 10 were 1920 mm$^2$. In this experiment, the motor surface temperature without the heat-conductive elastic members 28 sandwiched between the motor 8 and the retaining member 10 increased to 63.7° C. while the motor surface temperature with the heat-conductive elastic members 28 sandwiched increased only to 58.3° C. In other words, because the heat of the motor 8 was radiated to the retaining member 10 through the heat-conductive elastic members 28, the temperature of the motor 8 could be reduced by 5.4° C.

The surface temperature of the motor influences longevity and performance of the motor. From a viewpoint of the longevity of the motor, it is preferable to maintain the surface temperature of the motor at 60° C. or lower in the case of the motor used in the experiment. By maintaining the surface temperature at 60° C. or lower, it is possible to extend the longevity to about 15 years.

The motor surface temperature increased to 63.7° C. when the heat-conductive elastic members 28 were not sandwiched between the motor 8 and the retaining member 10 under the conditions of the above experiment and therefore it is preferable to reduce the motor surface temperature by 3.7° C. or more. If the heat-conductive elastic members 28 are sandwiched as described in the above embodiment, heat radiation from the motor 8 to the retaining member 10 through the heat-conductive elastic members 28 is known to be $2.8 \times 10^{-3}$° C. per 1 mm². Therefore, in order to reduce the motor surface temperature by 3.7° C. or more, it is preferable that the contact area between the heat-conductive elastic members 28 and the motor fixing portion 20 and the contact area between the heat-conductive elastic members 28 and the retaining member 10 are 1316 mm² or greater. In the experiment, the contact area of the heat-conductive elastic members 28 was 1920 mm² and therefore sufficient heat was radiated from the motor 8 to the retaining member 10, which maintains the surface temperature of the motor 8 at 60° C. or lower to prevent shortening of its longevity.

What is claimed is:

1. A solution sending pump comprising:
   a pump head including a pump chamber and a solution inlet and outlet for drawing and discharging a solution into and out of the pump chamber;
   a plunger having a tip end inserted into the pump chamber and for sliding in the pump chamber;
   a driving portion including a motor for driving the plunger and a driving transmitting portion for converting rotary movement of the motor into reciprocating movement in a certain direction to transmit the movement to the plunger; and
   a retaining member made of heat-conductive material and for retaining the driving portion,
   wherein the motor is fixed to the retaining member with a clearance between a main body portion of the motor and the retaining member,
   the motor main body portion and the retaining member are fixed to each other by a well nut and a screw,
   the clearance is defined by a thickness of a flange portion of the well nut, and
   a heat-conductive elastic member is inserted into the clearance,
   wherein the motor and the driving portion are coupled indirectly to each other, and
   wherein a face of the motor main body portion facing the retaining member is planar and square, the motor main body portion and the retaining member are fixed to each other at four corner portions of the square, and the elastic member comprises a plurality of pieces and each piece is inserted adjacent to and along a respective side of the square, the elastic member being sandwiched between the planar and square face of the motor main body portion and the retaining member.

2. The solution sending pump according to claim 1, wherein the retaining member is an aluminum die-cast product, and
   the elastic member is made of low-molecular siloxane resin.

\* \* \* \* \*